United States Patent
Zechlin et al.

(10) Patent No.: US 7,057,071 B2
(45) Date of Patent: Jun. 6, 2006

(54) PROCESS FOR PRODUCING 5-NITRO-3,4-DIHYDRO-1(2H)-NAPHTHALINONE, 1-5-NAPHTHALENEDIAMINE AND 1,5-NAPHTHALENE DIISOCYANATE

(75) Inventors: Joachim Zechlin, Neuss (DE); Kai Verkerk, Hilden (DE); Dietmar Wastian, Dormagen (DE); Katrin Joschek, Köln (DE); Tim Loddenkemper, Dormagen (DE); Wilfried Pinke, Dormagen (DE); Michael Schelhaas, Köln (DE); Georg Ronge, Düsseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 273 days.

(21) Appl. No.: 10/446,319

(22) Filed: May 28, 2003

(65) Prior Publication Data

US 2003/0229252 A1    Dec. 11, 2003

(30) Foreign Application Priority Data

Jun. 3, 2002    (DE) ............................... 102 24 463

(51) Int. Cl.
    *C07C 209/36*    (2006.01)
(52) U.S. Cl. ..................................... 564/308
(58) Field of Classification Search ................ 564/308
    See application file for complete search history.

(56) References Cited

U.S. PATENT DOCUMENTS

| 3,448,139 | A | 6/1969 | Farrissey, Jr. et al. ...... 260/465 |
| 4,973,758 | A | 11/1990 | Behre et al. ................ 564/394 |
| 6,737,548 | B1 * | 5/2004 | Inoki et al. ................. 564/308 |
| 2002/0103401 | A1 | 8/2002 | Schelhaas et al. .......... 564/415 |

FOREIGN PATENT DOCUMENTS

| DE | 196 51 041 | 6/1998 |
| EP | 1 295 864 | 3/2003 |
| GB | 1 499 699 | 2/1978 |
| GB | 1 543 276 | 3/1979 |
| JP | 56-59738 | 5/1981 |
| JP | 4-154745 | 5/1992 |
| JP | 7-278066 | 10/1995 |
| WO | WO 02/090315 A1 * | 11/2002 |

* cited by examiner

*Primary Examiner*—Samuel Barts
(74) *Attorney, Agent, or Firm*—Joseph C. Gil; Lyndanne M. Whalen; John E. Mrozinski, Jr.

(57) ABSTRACT

The present invention relates to a process for producing 5-nitro-3,4-dihydro-1(2H)-naphthalinone, 1,5-naphthalene-diamine and 1,5-naphthalene diisocyanate, in which 4-(2-nitrophenyl)-n-butyronitrile is converted to 4-(2-nitrophenyl)-n-butyric acid.

7 Claims, No Drawings

PROCESS FOR PRODUCING 5-NITRO-3,4-DIHYDRO-1(2H)-NAPHTHALINONE, 1-5-NAPHTHALENEDIAMINE AND 1,5-NAPHTHALENE DIISOCYANATE

FIELD OF THE INVENTION

This invention relates to a process for producing 5-nitro-3,4-dihydro-1(2H)-naphthalinone by hydrolysis of 4-(2-nitrophenyl)-n-butyronitrile and by reaction of the 4-(2-nitrophenyl)-n-butyric acid formed therefrom.

BACKGROUND OF THE INVENTION 5-nitro-3,4-dihydro-1(2H)-naphthalinone is an intermediate for the production of 1,5-naphthalenediamine, which can be obtained from 5-nitro-3,4-dihydro-1(2H)-naphthalinone by amination, aromatization and subsequent hydrogenation. 1,5-naphthalenediamine can be further reacted with phosgene to form 1,5-naphthalene diisocyanate.

Various processes for producing 1,5-naphthalenediamine are already known in the literature. In general, the preparation of 1,5-naphthalenediamine starts from naphthalene, which is suitably substituted. Thus, in JP-A2-07 278 066, the synthesis of 1,5-naphthalenediamine via an amine-bromine exchange in 1,5-bromoaminonaphthalene is described. In this process, the required educt is produced by bromination of 1-nitronaphthalene.

In JP-A2-04 154 745, JP-A2-56 059 738 and DE-A1-2 523 351, the synthesis of 1,5-naphthalenediamine in combination with 1,8-naphthalenediamine by reduction of a mixture of 1,5- and 1,8-dinitronaphthalene is described. The synthesis of 1,5-bromoaminonaphthalene by alkaline hydrolysis of disodium naphthalene-1,5-disulfonate and subsequent reaction with ammonia is described in DE-C1-3 840 618.

All the above-described processes have the disadvantage that the product, or an intermediate product produced in the course of the process, is obtained in the form of a mixture of isomers which in addition to the 1,5-isomers contains further isomers which have to be separated off. Moreover, the process described in DE-C1-3 840 618, in particular, proceeds under very drastic and corrosive reaction conditions.

SUMMARY OF THE INVENTION

Accordingly, the present invention provides a simple process for preparing intermediates for the production of 1,5-naphthalenediamine, whereby the 1,5-naphthalenediamine can be produced without the formation of significant amounts of other isomers, which have to be separated off. The present invention also provides a process for producing 1,5-naphthalenediamine and 1,5-naphthalene diisocyanate, based on these intermediates.

DETAILED DESCRIPTION OF THE INVENTION

A process has now been found whereby, starting from 4-(2-nitrophenyl)-n-butyronitrile, it is possible to prepare 5-nitro-3,4-dihydro-1(2H)-naphthalinone easily and in largely isomerically pure form as an intermediate for the production of 1,5-naphthalenediamine.

The present invention relates to a process for producing 5-nitro-3,4-dihydro-1(2H)-naphthalinone, in which 4-(2-nitrophenyl)-n-butyronitrile is converted to 4-(2-nitrophenyl)-n-butyric acid.

4-(2-nitrophenyl)-n-butyronitrile can be prepared from ortho-nitrotoluene and acrylonitrile, preferably at temperatures of −10° C. to 100° C. The reaction is conducted more preferably at 20° C. to 75° C., most preferably at temperatures of 30° C. to 60° C.

The reaction is carried out using base catalysis. Oxides, hydroxides and carbonates of lithium, sodium, potassium, rubidium, cesium, magnesium, calcium, strontium, barium or aluminum, as well as mixtures thereof, can be used as bases. Sodium hydroxide and potassium hydroxide are particularly preferred. It is preferable to use solutions of the base. The solutions of the base may also be used in combination with a phase transfer catalyst. Examples of such phase transfer catalysts are quaternary ammonium salts. Suitable ammonium compounds include, but are not limited to, tetraalkylammonium halides and tetraalkylammonium hydrogen sulfates, such as tributylmethylammonium chloride, trioctylammonium chloride, tetrabutylammonium chloride or tetrabutylammonium hydrogen sulfate. Equally suitable is the use of corresponding tetraalkyl- or tetraarylphosphonium salts, such as tetramethylphosphonium bromide and tetraphenylphosphonium bromide, as well as the use of solubilizers such as polyethylene glycol dimethyl ethers.

The solutions of the base are preferably used without a phase transfer catalyst.

Water and all base-resistant organic solvents are, in principle, suitable for use as solvents. Preferably used solvents are aromatic solvents, such as benzene, toluene, xylene, monochlorobenzene, dichlorobenzene, trichlorobenzene, nitrobenzene or nitrotoluene, as well as dimethyl sulfoxide, dimethylformamide and aliphatic hydrocarbons, such as ligroin, cyclohexane, pentane, hexane, heptane, octane. Dimethyl sulfoxide is used preferably in a concentration of 10–80 wt. %, based on ortho-nitrotoluene, more preferably in a concentration of 30–60 wt. %.

Ortho-nitrotoluene is preferably used in excess. Preferably 1 to 40 moles of ortho-nitrotoluene and more preferably 5 to 20 moles of ortho-nitrotoluene is used per mole of acrylonitrile.

In one embodiment of the present invention, the process for producing 5-nitro-3,4-dihydro-1(2H)-naphthalinone contains the steps:

a) reaction of 4-(2-nitrophenyl)-n-butyronitrile with an acid or with a base to produce 4-(2-nitrophenyl)-n-butyric acid, and b) cyclization of the 4-(2-nitrophenyl)-n-butyric acid formed in step a) to produce 5-nitro-3,4-dihydro-1(2H)-naphthalinone.

The hydrolysis of 4-(2-nitrophenyl)-n-butyronitrile to 4-(2-nitrophenyl)-n-butyric acid is carried out without solvent or in a solvent, in the presence of one or more acids or of one or more bases.

Suitable acids include, but are not limited to, strong acids, such as dilute or concentrated mineral acids such as hydrochloric acid, sulfuric acid, phosphoric acid, as well as hydrogen sulfates and dihydrogen phosphates.

Suitable bases include, but are not limited to, strong bases, such as oxides, hydroxides and carbonates of lithium, sodium, potassium, rubidium, cesium, magnesium, calcium, strontium, barium or aluminum as well as mixtures thereof, as well as aqueous solutions or suspensions of hydroxides and carbonates of lithium, sodium, potassium, rubidium, cesium, magnesium, calcium, strontium, barium or aluminum. Aqueous solutions of sodium hydroxide or potassium hydroxide are particularly suitable.

Suitable solvents include, but are not limited to, linear, branched or cyclic aliphatic hydrocarbons, such as ligroin or cyclohexane, pentane, hexane, heptane, octane, as well as aromatic solvents, such as benzene, toluene, xylene, monochlorobenzene, dichlorobenzene, trichlorobenzene. The procedure is preferably solventless.

Preferably 0.5 to 20 moles of acid or base, more preferably 1 to 10 moles of acid or base and most preferably 1.5 to 6 moles of acid or base is used per mole of 4-(2-nitrophenyl)-n-butyronitrile.

The reaction is carried out preferably at temperatures of 0° C. to 150° C., more preferably between 30° C. and 120° C. and most preferably between 50° C. and 100° C.

The cyclization of 4-(2-nitrophenyl)-n-butyric acid to 5-nitro-3,4-dihydro-1(2H)-naphthalinone is carried out without solvent or in a solvent, in the presence of one or more acids. Suitable acids include, but are not limited to, strong Lewis or Bronsted acids such as, for example, aluminum trichloride, boron trifluoride, sulfuric acid, phosphoric acid, polyphosphoric acid, phosphorus pentoxide, methanesulfonic acid, trifluoromethanesulfonic acid, trifluoroacetic acid, niobic acid or mixtures of antimony pentafluoride and fluorosulfuric acid. Mixtures of acids may also be used. Heterogenized acids may also be used, for example, polyphosphoric acid or partly fluorinated or perfluorinated aryl- or alkylsulfonic acids on supports such as silicon dioxide, dialuminum trioxide or even partly fluorinated or perfluorinated polymeric aryl- or alkylsulfonic acids.

Preferably 0.1 to 100 moles of acid, more preferably 0.5 to 50 moles of acid and most preferably 1 to 25 moles of acid is used per mole of 4-(2-nitrophenyl)-n-butyric acid.

The reaction is carried out preferably at temperatures of 50° C. to 300° C., more preferably between 100° C. and 250° C. and most preferably between 120° C. and 230° C.

Suitable solvents include, but are not limited to, linear, branched or cyclic aliphatic hydrocarbons, such as ligroin or cyclohexane, pentane, hexane, heptane, octane, aromatic solvents, such as benzene, toluene, xylene, monochlorobenzene, dichlorobenzene, trichlorobenzene, solvents such as dimethyl sulfoxide, dimethylformamide, as well as high-boiling alkylbenzene derivatives or benzene derivatives which are stable at high temperatures, such as isomeric dibenzyltoluenes, di- and triarylalkyls, bi- or triaryloxides, terphenyls and partially hydrogenated and hydrogenated analogues thereof, alkylated or non-alkyl-substituted benzyltoluenes. A solventless procedure is also possible.

All the reaction steps may be carried out continuously or batchwise, for example, in stirred-tank reactors or in tubular reactors.

In another embodiment of the present invention, the process for producing 5-nitro-3,4-dihydro-1(2H)-naphthalinone contains the steps:
a) reaction of 4-(2-nitrophenyl)-n-butyronitrile with an acid or with a base to produce 4-(2-nitrophenyl)-n-butyric acid,
b) chlorination of the 4-(2-nitrophenyl)-n-butyric acid formed in step a) to produce 4-(2-nitrophenyl)-n-butyryl chloride, and
c) cyclization of the 4-(2-nitrophenyl)-n-butyryl chloride formed in step b) to produce 5-nitro-3,4-dihydro-1(2H)-naphthalinone.

The reaction (hydrolysis) of 4-(2-nitrophenyl)-n-butyronitrile with an acid or with a base to produce 4-(2-nitrophenyl)-n-butyric acid, similarly to step a) of the first described embodiment, is carried out without solvent or in a solvent, in the presence of one or more acids or of one or more bases.

Suitable acids include, but are not limited to, strong acids, such as dilute or concentrated mineral acids such as hydrochloric acid, sulfuric acid, phosphoric acid, as well as hydrogen sulfates and dihydrogen phosphates.

Suitable bases include, but are not limited to, strong bases, such as oxides, hydroxides and carbonates of lithium, sodium, potassium, rubidium, cesium, magnesium, calcium, strontium, barium or aluminum as well as mixtures of these, as well as aqueous solutions or suspensions of hydroxides and carbonates of lithium, sodium, potassium, rubidium, cesium, magnesium, calcium, strontium, barium or aluminum. Aqueous solutions of sodium hydroxide or potassium hydroxide are particularly suitable.

Suitable solvents include, but are not limited to, linear, branched or cyclic aliphatic hydrocarbons, such as ligroin or cyclohexane, pentane, hexane, heptane, octane, as well as aromatic solvents, such as benzene, toluene, xylene, monochlorobenzene, dichlorobenzene, trichlorobenzene. The procedure is preferably solventless.

Preferably 0.5 to 20 moles of acid or base, more preferably 1 to 10 moles of acid or base and most preferably 1.5 to 6 moles of acid or base is used per mole of 4-(2-nitrophenyl)-n-butyronitrile.

The reaction is carried out preferably at temperatures of 0° C. to 150° C., more preferably between 30° C. and 120° C. and most preferably between 50° C. and 100° C.

The chlorination of 4-(2-nitrophenyl)-n-butyric acid to 4-(2-nitrophenyl)-n-butyryl chloride is carried out using chlorinating agents such as chlorine, thionyl chloride, phosgene, phosphoryl chloride, phosphorus trichloride or phosphorus pentachloride. Preferably thionyl chloride or phosgene is used.

Suitable solvents include, but are not limited to, linear, branched or cyclic aliphatic hydrocarbons, such as ligroin or cyclohexane, pentane, hexane, heptane, octane, as well as aromatic solvents, such as benzene, xylene, monochlorobenzene, dichlorobenzene, trichlorobenzene. The procedure is preferably solventless.

The reaction is carried out preferably at temperatures of 0° C. to 250° C., more preferably between 20° C. and 200° C. and most preferably between 30° C. and 180° C.

The cyclization of the 4-(2-nitrophenyl)-n-butyryl chloride formed in step b) to produce 5-nitro-3,4-dihydro-1(2H)-naphthalinone is carried out without solvent or in a solvent, in the presence of acids. Suitable acids include, but are not limited to, strong Lewis or Bronsted acids such as, for example, aluminum trichloride, iron trichloride, tin dichloride, titanium tetrachloride, boron trifluoride, sulfuric acid, phosphoric acid, polyphosphoric acid, phosphorus pentoxide, methanesulfonic acid, trifluoromethanesulfonic acid, trifluoroacetic acid, niobic acid or mixtures of antimony pentafluoride and fluorosulfuric acid. Mixtures of acids may also be used. Heterogenized acids may also be used, for example, polyphosphoric acid or partly fluorinated or perfluorinated aryl- or alkylsulfonic acids on supports such as silicon dioxide, dialuminum trioxide or even partly fluorinated or perfluorinated polymeric aryl- or alkylsulfonic acids.

Suitable solvents include, but are not limted to, linear, branched or cyclic aliphatic hydrocarbons, such as ligroin or cyclohexane, pentane, hexane, heptane, octane, aromatic solvents, such as monochlorobenzene, dichlorobenzene, trichloro-benzene, solvents such as dimethyl sulfoxide, dimethylformamide, as well as high-boiling alkylbenzene derivatives or benzene derivatives which are stable at high temperatures, such as isomeric dibenzyltoluenes, di- and triarylalkyls, bi- or triaryloxides, terphenyls and partially hydrogenated and hydrogenated analogues thereof, alkylated or non-alkyl-substituted benzyltoluenes. A solventless procedure is also possible.

Preferably 0.1 to 100 moles of acid, more preferably 0.5 to 50 moles of acid and most preferably 1 to 25 moles of acid is used per mole of 4-(2-nitrophenyl)-n-butyryl chloride.

The reaction is carried out preferably at temperatures of 50° C. to 300° C., more preferably between 100° C. and 250° C. and most preferably between 120° C. and 230° C.

All the reaction steps may be carried out continuously or batchwise, for example, in stirred-tank reactors or in tubular reactors.

The invention relates also to a process for producing 1,5-naphthalenediamine, in which 4-(2-nitrophenyl)-n-butyronitrile is converted to 4-(2-nitrophenyl)-n-butyric acid.

1,5-naphthalenediamine is obtained by amination, aromatization and hydrogenation, starting from 5-nitro-3,4-dihydro-1(2H)-naphthalinone.

The amination of 5-nitro-3,4-dihydro-1(2H)-naphthalinone to the nitroimine or nitroenamine is effected by reaction with ammonia, preferably in the presence of ammonium salts such as ammonium chloride.

The aromatization or dehydrogenation of the nitroenamine 5-nitro-3,4-dihydro-1-naphthylamine or of the nitroimine 5-nitro-3,4-dihydro-1(2H)-naphthylimine to 5-nitro-1-naphthylamine or 5-nitroso-1-naphthylamine or to a mixture of the compounds is carried out, for example, in an inert solvent without catalyst or in the presence of a catalyst. Here, in addition to the dehydrogenated product 5-nitro-1-naphthylamine, 5-nitroso-1-naphthylamine may also be produced formally by synproportionation. Traces of 1,5-naphthalenediamine are also formed. The products can be further processed in any mixing ratios.

Suitable solvents include, but are not limited to, ammonia and linear, branched or cyclic aliphatic hydrocarbons, such as ligroin or cyclohexane, as well as acetonitrile, dimethylformamide, dimethylacetamide and aromatic solvents, such as benzene, toluene, xylene, nitrobenzene, nitrotoluene or monochlorobenzene, dichlorobenzene, trichlorobenzene. The aromatization may also be carried out in the absence of a solvent.

Suitable catalysts include, but are not limited to, dehydrogenation catalysts, which are described in the literature (Römpp Lexikon Chemie, Georg Thieme Verlag, Stuttgart, 10th Edition 1997, p. 891, Chapter entitled "Dehydrogenation", 1st section; Ullmann's Encyclopedia of Industrial Chemistry, VCH Verlagsgesellschaft mbH, Weinheim, 5th Edition 1989, Vol A13, Chapter entitled "Hydrogenation and Dehydrogenation", Subchapter 2 "Dehydrogenation", p. 494–497). These include the metals of the eighth to the tenth groups of the periodic table (G. J. Leigh [Editor], Nomenclature of Inorganic Chemistry, Recommendations 1990, Blackwell Scientific Publications, Oxford, Chapter I-3.8.1. "Groups of Elements in the Periodic Table and their Subdivision", p. 41–43), in particular platinum, palladium, ruthenium and iridium, iron, cobalt, nickel and combinations thereof. The metals may also be used together with other metals, such as lanthanum, scandium, vanadium, chromium, molybdenum, tungsten, manganese, tin, zinc, copper, silver or indium. Here, the above-mentioned metals may also be present as pure elements, as oxides, sulfides, halides, carbides or nitrides, or else may be used combined with organic ligands. Hydrocarbon compounds having donor groups such as, for example, amines, nitrites, phosphines, thiols, thioethers, alcohols, ethers or carboxylic acids are suitable as ligands. The catalysts may optionally be applied to a support. Suitable supports are activated carbon, aluminum oxide, silicon oxide, zirconium oxide, zinc oxide, zeolites.

Optionally, the procedure may be conducted in the presence of an oxidizing agent such as oxygen or air. The reaction is preferably carried out at temperatures of 50° C. to 250° C., more preferably at 100° C. to 200° C.

The subsequent hydrogenation of 5-nitro-1-naphthylamine or 5-nitroso-1-naphthylamine, or of a mixture of the compounds, to 1,5-naphthalenediamine is carried out in the presence of a hydrogenation catalyst.

Suitable hydrogenation catalysts include virtually all heterogeneous catalysts which are known to be hydrogenation catalysts (Römpp Lexikon Chemie, Georg Thieme Verlag, Stuttgart, 10th Edition 1997, p. 1831, Chapter entitled "Hydrogenation"; Ullmann's Encyclopedia of Industrial Chemistry, VCH Verlagsgesellschaft mbH, Weinheim, 5th Edition 1989, Vol A13, Chapter entitled "Hydrogenation and Dehydrogenation", Subchapter 1.2 "Catalysts", p. 488). Preferred catalysts are the metals of the eighth to the tenth groups of the periodic table (G. J. Leigh [Editor], Nomenclature of Inorganic Chemistry, Recommendations 1990, Blackwell Scientific Publications, Oxford, Chapter I-3.8.1. "Groups of Elements in the Periodic Table and their Subdivision", p. 41–43), copper or chromium on a suitable support preferably having a metal content of 0.01 wt. %, to 50 wt. %, more preferably 0.1 wt. %, to 20 wt. %, based on the total weight of the catalyst. Catalysts containing one or more of the above-mentioned metals may also be used. Preferred metals are in particular platinum, palladium and rhodium; platinum and palladium are particularly preferred. Other preferred catalysts are Raney nickel and supported nickel catalysts. The above-mentioned metals or their compounds may also be used in pure form as solid substances. Examples of a metal in pure form are palladium black and platinum black.

In variants of the batch process, the catalysts may preferably be used in quantities of 0.01 wt. %, to 50 wt. %, based on 5-nitro-1-naphthylamine or 5-nitroso-1-naphthylamine, more preferably in quantities of 0.01 wt. %, to 20 wt. %, most preferably in quantities of 0.01 wt. %, to 10 wt. %. Where the reaction is carried out continuously, for example, in a stirred-tank reactor using a pulverulent catalyst or in the trickle phase on a fixed-bed catalyst, loading rates of 0.01 g to 500 g, preferably 0.1 g to 200 g, more preferably 1 g to 100 g, of 5-nitro-1-naphthylamine or 5-nitroso-1-naphthylamine per gram of catalyst per hour may be established.

The reaction temperatures are preferably −20° C. to 150° C., more preferably 40° C. to 120° C.; the hydrogen pressure is preferably 0.1 to 150 bar, more preferably 0.5 to 70 bar, most preferably 1 to 50 bar.

Preferably the same catalyst may be used for the aromatization (dehydrogenation) and for the subsequent hydrogenation, the two steps possibly being carried out in succession in one reaction vessel.

Suitable solvents for the hydrogenation include, but are not limited to, linear or branched aliphatic alcohols, such as methanol, ethanol, propanol, butanol, linear, branched or cyclic aliphatic hydrocarbons, such as ligroin or cyclohexane, as well as dimethylformamide, dioxan, dimethylacetamide and aromatic solvents, such as benzene, toluene, xylene, nitrobenzene, nitrotoluene or monochlorobenzene, dichlorobenzene, trichlorobenzene.

The 1,5-naphthalenediamine obtained by the processes of the present invention can be phosgenated in a known manner to the 1,5-naphthalene diisocyanate.

The invention is further illustrated but is not intended to be limited by the following examples in which all parts and percentages are by weight unless otherwise specified.

EXAMPLES

Example 1

Preparation of 4-(2-nitrophenyl)-n-butyric acid by hydrolysis of 4-(2-nitrophenyl)-n-butyronitrile using phosphoric acid 190 g 4-(2-nitrophenyl)-n-butyronitrile (1 mol) and 1153 g phosphoric acid (85 wt. %) (10 mol) were placed in a 2 l four-necked stirring flask equipped with paddle stirrer, thermometer and condenser. The reaction mixture was heated to 100° C., with stirring, and stirred at 100° C. for 17 hours. The reaction mixture was slowly cooled to room temperature, with stirring, during which the emulsified 4-(2-nitrophenyl)-n-butyric acid solidified. The excess phosphoric acid was decanted and the solid matter was dissolved in 1000 ml chloroform. The solution was transferred to a separatory funnel and washed three times, each time with 50 ml distilled water, to free it of phosphorus and evaporated to small bulk in a rotary evaporator at 80° C. and 20 mbar. The residue (4-(2-nitrophenyl)-n-butyric acid) was crushed and dried to constant mass over diphosphorus pentoxide in a desiccator.

The decanted phosphoric acid was diluted with 2 l distilled water and extracted with 500 ml chloroform. The chloroform extract was evaporated to small bulk in a rotary evaporator at 80° C. and 20 mbar and the residue (4-(2-nitrophenyl)-n-butyric acid) was combined with the residue from the drying.

Final weight of 4-(2-nitrophenyl)-n-butyric acid: 200.2 g, corresponding to 95.8% crude yield (purity: 99.3%, determined by gas chromatography (GC)).

Example 2

Preparation of 5-nitro-3,4-dihydro-1(2H)-naphthalinone by cyclisation of 4-(2-nitrophenyl)-n-butyric acid, using phosphoric acid 50 g dibenzyltoluene (mixture of isomers, trade name MARLOTHERM SH, Sasol Germany GmbH) and 10 g polyphosphoric acid (85 wt. % $P_4O_{10}$) were placed in a two-necked flask equipped with magnetic stirrer, still head, vacuum receiver, receiving flasks and heatable addition funnel. The addition funnel, heated to 90° C., was charged with a solution of 2 g 4-(2-nitrophenyl)-n-butyric acid (NPBS, 9.57 mmol) in 20 g dibenzyltoluene (mixture of isomers, trade name MARLOTHERM SH, Sasol Germany GmbH). The apparatus was evacuated and heated to reflux temperature, with stirring (163° C., 0.2 mbar). The solution was continuously added dropwise, over a period of 20 minutes. The withdrawal of the distillate was adjusted to the feed, so that the volume of the reaction in the bottom flask remained constant. When all the solution had been added, the mixture was rewashed with 20 g dibenzyltoluene (mixture of isomers, trade name MARLOTHERM SH, Sasol Germany GmbH) and distilled clean.

The distillate contained 626 g 5-nitro-3,4-dihydro-1(2H)-naphthalinone (NT) and 1268 g NPBS (determined by GC/internal-standard method):

| | |
|---|---|
| Yield NT: | 34.2% |
| Conversion of NPBS: | 36.8% |
| Selectivity: | 93.1% |

Example 3

Preparation of 5-nitro-3,4-dihydro-1(2H)-naphthalinone by cyclization of 4-(2-nitrophenyl)-n-butyric acid, using trifluoromethanesulfonic acid 1 g 4-(2-nitrophenyl)-n-butyric acid (NPBS, 4.78 mmol) and 18 g trifluoromethanesulfonic acid (TFMA) (119.9 mmol), at 20° C., were placed in a 100 ml two-necked flask equipped with reflux condenser and magnetic stirrer. The solution was heated, with stirring, on an oil bath previously heated to 130° C., then stirred at 130° C. for 45 minutes. The solution was cooled and transferred to a microdistillation apparatus. The bulk of the excess TFMA was distilled off at an overhead temperature of 52° C. and 0.5 mbar. The bottom of the column contained 0.914 g 5-nitro-3,4-dihydro-1(2H)-naphthalinone and 3.44 g TFMA (determined by GC-ISTD/internal-standard method):

| | |
|---|---|
| Yield NT: | 99.3% |
| Conversion of NPBS: | 100 % |
| Selectivity: | 99.3% |

Example 4

Preparation of 4-(2-nitrophenyl)-n-butyryl chloride by chlorination of 4-(2-nitrophenyl)-n-butyric acid using thionyl chloride 744.3 g 4-(2-nitrophenyl)-n-butyric acid (NPBA, 3.56 mol) was placed in a 4 l four-necked stirring flask equipped with paddle stirrer, thermometer, condenser and drying pistol. 635.5 g thionyl chloride (5.34 mol) was added dropwise, with stirring, at room temperature. In the course of this addition, the temperature fell to −6° C. The reaction mixture was slowly heated to reflux temperature (max. 80° C.) by means of a mushroom heater. In the course of this heating, a reddish-brown, slightly viscous liquid formed, accompanied by a vigorous evolution of gas. The reaction mixture was stirred for an hour under reflux conditions. The excess thionyl chloride was distilled off at 80° C. under a water jet vacuum. The acid chloride was purified by flash distillation in a hot-air distillation apparatus (260° C. hot air, temperature at bottom of column <180° C., pressure <1 mbar).

Distillate: 767.7 g 4-(2-nitrophenyl)-n-butyryl chloride, corresponding to 94.8% crude yield (purity: 92.7%, determined by GC).

Example 5

Preparation of 4-(2-nitrophenyl)-n-butyryl chloride by chlorination of 4-(2-nitrophenyl)-n-butyric acid using phosgene 20 g 4-(2-nitrophenyl)-n-butyric acid (95.7 mmol) was dissolved in 180 g 1,2,4-trichlorobenzene at 35° C. in a 250 ml four-necked flask equipped with stirrer, thermometer and condenser (with connection to a phosgene destruction tower). Phosgene was introduced at a rate of 100 g/h through an immersed glass tube. The reaction mixture was heated to 180° C. over a period of 20 minutes and chlorinated for 2 hours with phosgene at a rate of 100 g/h, with stirring throughout. The deep orange-brown colored solution was dephosgenated by stripping with nitrogen at 100° C. The 1,2,4-trichlorobenzene was distilled off in a hot-air distillation apparatus (140° C. temperature of hot air, pressure <1 mbar).

Residue: 21.3 g 4-(2-nitrophenyl)-n-butyryl chloride, corresponding to 97.7% crude yield (purity: 91.0%, determined by GC).

Example 6

Preparation of 5-nitro-3,4-dihydro-1(2H)-naphthalinone by cyclization of 4-(2-nitrophenyl)-n-butyryl chloride, using aluminium trichloride 762.2 g 4-(2-nitrophenyl)-n-butyryl chloride (from Example 4) was dissolved in 4.5 l carbon disulfide in a 10 l four-necked stirring flask equipped with paddle stirrer, thermometer, condenser, drying pistol and powder addition funnel. At 15° C., 535.8 g aluminum chloride (4.0 mol) was introduced through a powder addition funnel. In the course of this addition, the aluminum chloride passed almost completely into solution and the temperature at the bottom of the column rose to 30° C. After a short time two phases formed; the lower ketone-aluminum chloride complex phase was reddish-brown and oily. When the addition of the aluminum chloride was complete, stirring was continued at room temperature for a further 4 hours, during which time the oily phase solidified completely. The carbon disulfide was decanted and 2.6 l distilled water was added to the solid phase, with cooling, to decompose the ketone-aluminium chloride complex. The addition of 2.6 l dichloromethane accelerated the hydrolysis and completely dissolved the 5-nitro-3,4-dihydro-1(2H)-naphthalinone formed. The organic phase was washed three times with 1.4 l in total of distilled water, once with 1000 ml sodium hydroxide solution (1 wt. % NaOH) and subsequently with distilled water to neutralize it. The solution was evaporated to small bulk in a rotary evaporator and the precipitated 5-nitro-3,4-dihydro-1(2H)-naphthalinone was dried to constant mass over diphosphorus pentoxide in a desiccator.

Final weight: 548.5 g 5-nitro-3,4-dihydro-1(2H)-naphthalinone, corresponding to 85.7% crude yield (purity: 99.5%, determined by GC).

Example 7

Preparation of 5-nitro-3,4-dihydro-1(2H)-naphthalinone by cyclization of 4-(2-nitrophenyl)-n-butyryl chloride, using phosphoric acid 50 g dibenzyltoluene (mixture of isomers, trade name MARLOTHERM SH, Sasol Germany GmbH) and 10 g polyphosphoric acid (85 wt. % $P_4O_{10}$) were placed in a two-necked flask equipped with magnetic stirrer, still head, vacuum receiver, receiving flasks and heatable addition funnel. The addition funnel, heated to 90° C., was charged with a solution of 2.2 g 4-(2-nitrophenyl)-n-butyryl chloride (NPBC, 9.67 mmol) in 20 g dibenzyltoluene (mixture of isomers, trade name MARLOTHERM SH, Sasol Germany GmbH). The apparatus was evacuated and heated to reflux temperature, with stirring (166° C., 0.1 mbar). The solution of NPBC was then continuously added dropwise, over a period of 20 minutes, to the previously prepared solution of phosphoric acid and dibenzyltoluene (mixture of isomers, trade name MARLOTHERM SH, Sasol Germany GmbH). Directly after dropwise addition of the acid chloride solution had commenced, the pressure in the apparatus rose to approximately 2 mbar, owing to formation of gaseous hydrogen chloride. The withdrawal of the distillate was adjusted to the feed, so that the volume of the reaction in the bottom flask remained constant. When all the solution had been added, the mixture was rewashed with 20 g dibenzyltoluene (mixture of isomers, trade name MARLOTHERM SH, Sasol Germany GmbH) and distilled clean.

The distillate contained 783 mg 5-nitro-3,4-dihydro-1(2H)-naphthalinone (NT) and 642 mg NPBS (determined by GC/internal-standard method):

| | |
|---|---|
| Yield NT: | 42.7% |
| Conversion of NPBSC: | 71.0% |
| Selectivity: | 62.8% |

Although the invention has been described in detail in the foregoing for the purpose of illustration, it is to be understood that such detail is solely for that purpose and that variations can be made therein by those skilled in the art without departing from the spirit and scope of the invention except as it may be limited by the appended claims.

What is claimed is:

1. A process for producing 1,5-naphthalenediamine comprising the steps of:
    reacting 4-(2-nitrophenyl)-n-butyronitrile with an acid or a base to produce 4-(2-nitrophenyl)-n-butyric acid;
    optionally chlorinating the 4-(2-nitrophenyl)-n-butyric acid to produce 4-(2-nitrophenyl)-n-butyryl chloride;
    cyclizing the 4-(2-nitrophenyl)-n-butyric acid or the 4-(2-nitrophenyl)-n-butyryl chloride to produce 5-nitro-3,4-dihydro-1 (2H)-naphthalinone;
    aminating the 5-nitro-3,4-dihydro-1 (2H)-naphthalinone to produce 5-nitro-3,4-dihydro-1 (2H)-naphthylamine or the tautomeric 5-nitro-3,4-dihydro-1 (2H)-naphthylimine;
    aromatizing the 5-nitro-3,4-dihydro-1 (2H)-naphthylamine or the tautomeric 5-nitro-3,4-dihydro-1 (2H)-naphthylimine to produce 5-nitro-1-naphthylamine and/or 5-nitroso-1-naphthylamine; and
    hydrogenating the 5-nitro-1-naphthylamine and/or 5-nitroso-1-naphthylamine to produce 1,5-naphthalenediamine.

2. The process of claim 1, wherein the acid in the step of reacting is selected from the group consisting of hydrochloric acid, sulfuric acid, phosphoric acid, hydrogen sulfates and dihydrogen phosphates.

3. The process of claim 1, wherein the base in the step of reacting is selected from the group consisting of oxides, hydroxides and carbonates of lithium, sodium, potassium, rubidium, cesium, magnesium, calcium, strontium, barium or aluminum and mixtures thereof, aqueous solutions or suspensions of hydroxides and carbonates of lithium, sodium, potassium, rubidium, cesium, magnesium, calcium, strontium, barium or aluminum.

4. The process of claim 1, wherein the step of cyclization occurs in the presence of at least one member selected from the group consisting of aluminum trichloride, boron trifluoride, sulfuric acid, phosphoric acid, polyphosphoric acid, phosphorus pentoxide, methanesulfonic acid, trifluoromethanesulfonic acid, trifluoroacetic acid, niobic acid and mixtures of antimony pentafluoride and fluorosulfuric acid.

5. The process of claim 1, wherein the optional step of chlorination occurs in the presence of at least one chlorinating agent selected from the group consisting of chlorine, thionyl chloride, phosgene, phosphoryl chloride, phosphorus trichloride and phosphorus pentachloride.

6. The process of claim 1, wherein the step of amination occurs by reaction with ammonia, optionally in the presence of an ammonium salt.

7. The process of claim 1, wherein the 4-(2-nitrophenyl)-n-butyronitrile is prepared by reacting ortho-nitrotoluene and acrylonitrile in the presence of a base.

* * * * *